United States Patent [19]

Ishiguru et al.

[11] Patent Number: 4,489,082

[45] Date of Patent: Dec. 18, 1984

[54] FUNGICIDAL COMPOSITION

[75] Inventors: Yukio Ishiguru; Hirotaka Takano, both of Takarazuka; Yuji Funaki, Toyonaka, all of Japan

[73] Assignee: Sumitomo Chemical Company, Limited, Osaka, Japan

[21] Appl. No.: 483,615

[22] Filed: Apr. 11, 1983

[30] Foreign Application Priority Data

Apr. 20, 1982 [JP] Japan ................... 57-66488

[51] Int. Cl.$^3$ .................. A01N 43/48; A01N 43/64; A01N 43/72
[52] U.S. Cl. ........................... 424/269; 424/274
[58] Field of Search ............... 548/262; 424/269, 274

[56] References Cited

FOREIGN PATENT DOCUMENTS

EP53311 6/1982 Fed. Rep. of Germany .
2332707       France .
2046260 11/1980 United Kingdom .

OTHER PUBLICATIONS

The Merck Index; Ninth Edition, pp. 225 & 544; (1976).

Primary Examiner—Leonard Schenkman
Assistant Examiner—J. Lipovsky
Attorney, Agent, or Firm—Stevens, Davis, Miller & Mosher

[57] ABSTRACT

A fungicidal composition which comprises an inert carrier and as an active ingredient (E)-1-(2,4-dichlorophenyl)-4,4-dimethyl-2-(1,2,4-triazol-1-yl)-1-penten-3-ol and an N-haloalkylthioimide fungicide in the ratio of 1 to 0.1–20 by weight in a total amount of 0.1 to 99.9% by weight.

3 Claims, No Drawings

FUNGICIDAL COMPOSITION

The present invention relates to a fugicidal composition which comprises, as active ingredients, (E)-1-(2,4-dichlorophenyl)-4,4-dimethyl-2-(1,2,4-triazol-1-yl)-1-penten-3-ol (hereinafter referred to as Compound A) and a N-haloalkylthioimide fungicide selected from N-(trichloromethylthio)-4-cyclohexene-1,2-dicarboximide (hereinafter referred to as Captan), N-(1,1,2,2-tetrachloroethylthio)-4-cyclohexane-1,2-dicarboximide (hereinafter referred to as Captafol, and N-(trichlorothio)-phthalimide (hereinafter referred to as Folpet), and an inert carrier.

As described in The Pesticide Manual, 6th edition, pp. 281, 77, and 78, N-haloalkylthioimide fungicide are known as preventive agents for protecting fruits, vegetables, and other useful plants from various diseases. Although having resistance to rain and residual effect, these fungicides are not always satisfactory as protectants for controlling diseases, such as powdery mildews, of cereals. They are also unsatisfactory as curative fungicides.

As disclosed in U.K. Patent Application No. GB 2046260A, Compound A has sufficient controlling effect on powdery mildews and rusts of cereal plants, fruits, and vegetables, but not always on diseases, such as late blights and downy mildews, caused by phytopathogenic fungi belonging to Phycomycetes.

The object of this invention is to provide a preventive and/or curative fungicidal composition that can simultaneously control various plant diseases at the lowest possible doses and maintain its preventive and/or curative effect.

The above object and others are accomplished by providing a fungicidal composition comprising Compound A and a N-haloalkylthioimide fungicide in a ratio of 1:0.1-1:20, preferably 1:1-1:10, by weight as active ingredients.

The fungicidal composition of this invention has preventive and/or curative effect on the following plants (pathogens): Rice (*Pyricularia oryzae; Cochliobolus miyabeanus; Rhizoctonia solani*), wheat, barley, and the like (*Erysphe graminis* f. sp. *hordei*, f. sp. *tritici; Gibberella zeae; Puccinia striiformis, P. graminis, P. recondita, P. hordei; Typhula* sp., *Micronectriella nivalis; Ustilago tritici, U. nuda; Pseudocercosporella herpotrichoides; Rhynchosporium secalis; Septoria tritici; Leptosphaeria nodorum*), citrus (*Diaporthe citri; Elsinoe fawcetti; Penicillium digitatum, P. italicum*), apple (*Sclerotinia mali; Valsa mali; Podosphaera leucotricha; Alternaria mali; Venturia inaequalis, Phytophthora cactorum*), pear (*Venturia nashicola; Alternaria kikuchiana; Gymnosporangium haraeanum*), peach (*Sclerotinia cinerea; Cladosporium carpophilum; Phomopsis* sp.), grape (*Elsinoe ampelina; Glomerella cingulata; Uncinula necator; Phakopsora ampelopsidis, Plasmapara viticola*), persimmon (*Gloeosporium kaki; Cerocospora kaki, Mycosphaerella nawae*), melons (*Colletotrichum lagenarium; Sphaerotheca fuliginea; Mycosphaerella melonis, Pseudoperonospora cubensis*), tomato (*Alternaria solani; Cladosporium fulvum, Phytophthora capsici*), eggplant (*Phomopsis vexans; Erysiphe cichoracearum*), vegetables of rape family (*Alternaria japonica; Cercosporella brassicae, Peronospora brassicae*), stone-leek (*Puccinia allii*), soybean (*Cercospora kikuchii; Elsinoe glycines; Diaporthe phaseolorum* var. *sojae*), kidney bean (*Colletotrichum lindemuthianum*), peanut (*Mycosphaerella personatum; Cercospora arachidicola*), pea (*Erysiphe pisi*), potato (*Alternaria solani. Phytophthora infestans*), strawberry (*Sphaerotheca humuli*), tea (*Exobasidium reticulatum; Elsinoe leucospila*), tobacco (*Alternaria longipes; Erysiphe cichoracearum; Colletotrichum tabacum, Peronospora tabacina*), sugar beet (*Cercospora beticola*), rose (*Diplocarpon rosae; Sphaerotheca pannosa*), chrysanthemum (*Septoria chrysanthemi-indici; Puccinia horiana*), various crops (*Botrytis cinerea; Sclerotinia sclerotiorum*), and so forth.

Accordingly, the fungicidal composition of this invention is applied to paddy fields, wheat fields, other cereal or vegetable fields, orchards, tea gardens, meadows, lawns, etc.

The present fungicidal composition may be applied without mixing any other material, but usually in the form of wettable powder, flowable, granular, dust, or others prepared by mixing a solid carrier, liquid carrier, surfactant or other adjuvant. These various forms of compositions contain 0.1-99.9%, preferably 1-99%, by total weight of the active ingredients.

Solid carriers usable for the composition include fine powders or granules of kaolin, attapulgite clay, bentonite, acid clay, pyrophyllite, talc, diatomaceous earth, calcite, corn kernel meal, walnut shell meal, urea, ammonium sulfate, and synthetic hydrated silica. Usable liquid carriers include aromatic hydrocarbons such as xylene and methylnaphthalene; alcohols such as isopropanol, ethylene glycol, and cellosolve; ketones such as acetone, cyclohexanone, and isophorone; vegetable oils such as soybean oil and cotton seed oil; dimethylsulfoxide, acetonitrile, and water.

Surfactants to be used for emulsifying, dispersing, or wetting-spreading the fungicide include anionic surfactants such as alkyl sulfate salts, alkylsulfonate or arylsulfonate salts, dialkyl sulfosuccinate salts, polyoxyethylene alkyl aryl ether phosphate salts, and naphthalenesulfonic acid-formalin condensation product; and nonionic surfactants such as polyoxyethylene alkyl ethers, polyoxyethylenepolyoxypropylene block copolymer, sorbitan-fatty acid esters, and polyoxyethylene sorbitan-fatty acid esters. The adjuvants include ligninsulfonic acid salts, alginic acid salts, polyvinyl alcohol, gum arabic, CMC (carboxymethyl-cellulose), and PAP (isopropyl acidphosphate).

Formulating of the fungicidal composition of this invention is illustrated by the following Formulation Examples, wherein parts are by weight.

FORMULATION EXAMPLE 1

A wettable powder was formulated by good mixing and grinding of 5 parts of Compound A, 50 parts of Captafol, 3 parts of calcium ligninsulfonate, 2 parts of sodium lauryl sulfate, and 40 parts of synthetic hydrated silica.

FORMULATION EXAMPLE 2

A granular composition was formulated by good mixing and grinding of 0.5 part of Compound A, 2.5 parts of Folpet, 1 part of synthetic hydrated silica, 2 parts of calcium ligninsulfonate, 30 parts of bentonite, and 64 parts of kaolin, and thoroughly kneading the mixture in the presence of water, followed by granulating and drying.

FORMULATION EXAMPLE 3

Flowable granules were formulated by mixing 5 parts of Compound A, 20 parts of Captan, 3 parts of polyoxyethylenesorbitan monooleate, 3 parts of CMC, and 69 parts of water, and grinding the mixture in wet form to particle sizes of the active ingredients of 5µ or less.

FORMULATION EXAMPLE 4

A dust composition was formulated by thoroughly mixing and grinding 0.5 part of Compound A, 1.5 parts of Captafol, 88 parts of kaolin, and 10 parts of talc.

These fungicidal compositions are applied as such or after dilution with water, to leaves and stems (or stalks) by spraying or to soil as dusts or granulars by mixing therewith. Enforced fungicidal efficacy is expectable when these compositions are served in mixture with some other fungicides. They also can be applied in combination with an insecticide, acaricide, nematocide, herbicide, plant growth regulator, fertilizer, or soil quality improver.

The compositions of this invention are applied in doses generally of 1–1000 g, preferably of 10–500 g of the whole active ingredient per acre. When they are applied in the form of wettable powder or flowable granular dust, the total concentration of the active ingredients ranges from 0.001 to 1%, preferably from 0.01 to 0.5%, by weight. In the form of granules or dust, they are applied without dilution.

The plant-disease controlling effect of the composition of this invention is illustrated with reference to the following Test Examples. In some of the Examples, besides the present active ingredients, the following compound was employed as a comparative active ingredient:

Chlorothalonil, structural formula:

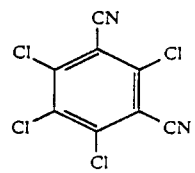

The effect was evaluated by visual observation of test plants to examine symptoms, viz. the growth extents of fungus colonies and of sick spots on the leaves and stems. Criteria of the evaluation are as follows:

Rating 5: None of said colonies and lesions were observed.
Rating 4: Said colonies and lesions were observed on about 10% of the leaves and stems.
Rating 3: They were observed on about 30% of the leaves and stems.
Rating 2: They were observed on about 50% of the leaves and stems.
Rating 1: They are observed on about 70% of the leaves and stems.
Rating 0: Symptoms were as remarkable as in the case of the control (no fungicide was applied).

TEST EXAMPLE 1

(Preventive effect on cucumber gray mold)

Cucumbers (var. Sagamihanjiro) were sowed in plastic pots filled with sand soil, and were grown for 8 days in a green house. Resulting cucumber seedlings, which had developed cotyledons, were sprayed with individual fungicidal flowable granules that had been formulated in accordance with Formulation Example 3 and diluted with water to predetermined concentrations. Then, agar pieces containing a cucumber gray mold fungus were attached to the seedlings to inoculate the fungus. The seedling were further grown for 3 days at 20° C. under a high humidity condition, to examine the controlling effect. The results are shown in Table 1.

TABLE 1

| Active ingredient | Concentration of active ingredient applied (ppm) | Controlling effect (rating) |
| --- | --- | --- |
| A | 10 | 0 |
| " | 50 | 2 |
| Captan | 40 | 1 |
| " | 50 | 2 |
| Captafol | 40 | 1 |
| " | 50 | 2 |
| Folpet | 40 | 1 |
| " | 50 | 2 |
| A + Captan | 10 + 40 | 5 |
| A + Captafol | 10 + 40 | 5 |
| A + Folpet | 10 + 40 | 5 |
| B | 100 | 3 |

TEST EXAMPLE 2

(Preventive effect on cucumber downy mildew)

Cucumbers (var. Sagami-hanjiro) were sowed in plastic pots filled with sand soil, and were grown for 14 days in a green house. Resulting seedlings, which had developed cotyledons, were sprayed with individual fungicidal flowable granules that had been formulated in accordance with Formulation Example 3 and diluted with water to predetermined concentrations. Then, a cucumber downy mildew fungus was inoculated upon the seedlings by spraying them with a suspension of its spores. The seedlings were further grown for 3 days at 20° C. under a high humidity condition and then for 3 days under illumination, to examine the controlling effect. The results are shown in Table 2.

TABLE 2

| Active ingredient | Concentration of active ingredient applied (ppm) | Controlling effect (rating) |
| --- | --- | --- |
| A | 10 | 0 |
| A | 50 | 1 |
| Captan | 40 | 3 |
| " | 50 | 3 |
| Captafol | 40 | 2 |
| " | 50 | 2 |
| Folpet | 40 | 2 |
| " | 50 | 3 |
| A + Captan | 10 + 40 | 5 |
| A + Captafol | 10 + 40 | 5 |
| A + Folpet | 10 + 40 | 5 |
| B | 100 | 3 |

TEST EXAMPLE 3

(Preventive effect on wheat leaf blight)

Wheat (var. Norin 73-go) was sowed in plastic pots filled with sand soil and was grown for 14 days in a green house. Resulting wheat seedlings, which had just developed the second leaf, were sprayed with individual fungicidal flowable granules that had been formulated in accordance with Formulation Example 3 and diluted with water to predetermined concentrations. Then, a wheat leaf blight fungus was inoculated upon the seedlings by spraying them with a suspension of its spores. The seedlings were further grown for 5 days at 18° C. under a high humidity condition and then for 14 days under illumination, to examine the controlling effect. The results are shown in Table 3.

TABLE 3

| Active ingredient | Concentration of active ingredient applied (ppm) | Controlling effect (rating) |
| --- | --- | --- |
| A | 2 | 0 |
| " | 10 | 3 |
| Captan | 8 | 1 |
| " | 10 | 2 |
| Captafol | 8 | 1 |
| " | 10 | 2 |
| Folpet | 8 | 1 |
| " | 10 | 1 |
| A + Captan | 2 + 8 | 5 |
| A + Captafol | 2 + 8 | 5 |
| A + Folpet | 2 + 8 | 5 |

TEST EXAMPLE 4

(Curative effect on wheat leaf blight)

Wheat (var. Norin 73-go) was sowed in plastic pots filled with sand soil and grown for 14 days in a green house. A wheat leaf blight fungus was inoculated upon resulting wheat seedlings, which had just developed the second leaf, by spraying them with a suspension of its spores. After further growth of the seedling for 5 days at 18° C. at a high humidity condition, individual fungicidal flowable granules that had been formulated in accordance with Formulation Example 3 and diluted with water to predetermined concentrations were sprayed to adhere sufficiently to the leaves of the seedlings. Thereafter, the seedlings were grown for 14 days at 18° C. under illumination to examine the controlling effect. The results are shown in Table 4.

TABLE 4

| Active ingredient | Concentration of active ingredient applied (ppm) | Controlling effect (rating) |
| --- | --- | --- |
| A | 50 | 4 |
| " | 10 | 3 |
| Captan | 50 | 0 |
| " | 40 | 0 |
| Captafol | 50 | 0 |
| " | 40 | 0 |
| Folpet | 50 | 0 |
| " | 40 | 0 |
| A + Captan | 10 + 40 | 5 |
| A + Captafol | 10 + 40 | 5 |
| A + Folpet | 10 + 40 | 5 |

What is claimed is:
1. A fungicidal composition which comprises an inert carrier and as an active ingredients (E)-1-(2,4-dichlorophenyl)-4,4-dimethyl-2-(1,2,4-triazol-1-yl)-1-penten-3-ol and an N-haloalkylthioimide fungicide selected from the group consisting of N-(trichloromethylthio)-4-cyclohexene-1,2-dicarboximide fungicide, N-(1,1,2,2-tetrachloroethylthio)-4-cyclohexane-1,2-dicarboximide fungicide and N-(trichloromethylthio)phthalimide fungicide in the ratio of 1:1 to 1:10 by weight in a total amount of 0.1 to 99.9% by weight of the composition.

2. The composition according to claim 1 wherein the total amount of (E)-1-(2,4-dichlorophenyl)-4,4-dimethyl-2-(1,2,4-triazol-1-yl)-1-penten-3-ol and N-haloalkylthioimide fungicide is 1 to 99% by weight.

3. A method for controlling a phytopathogenic fungi which comprises applying a fungicidally effective amount of the fungicidal composition according to claim 1 to fungi.

* * * * *